Figure 1:
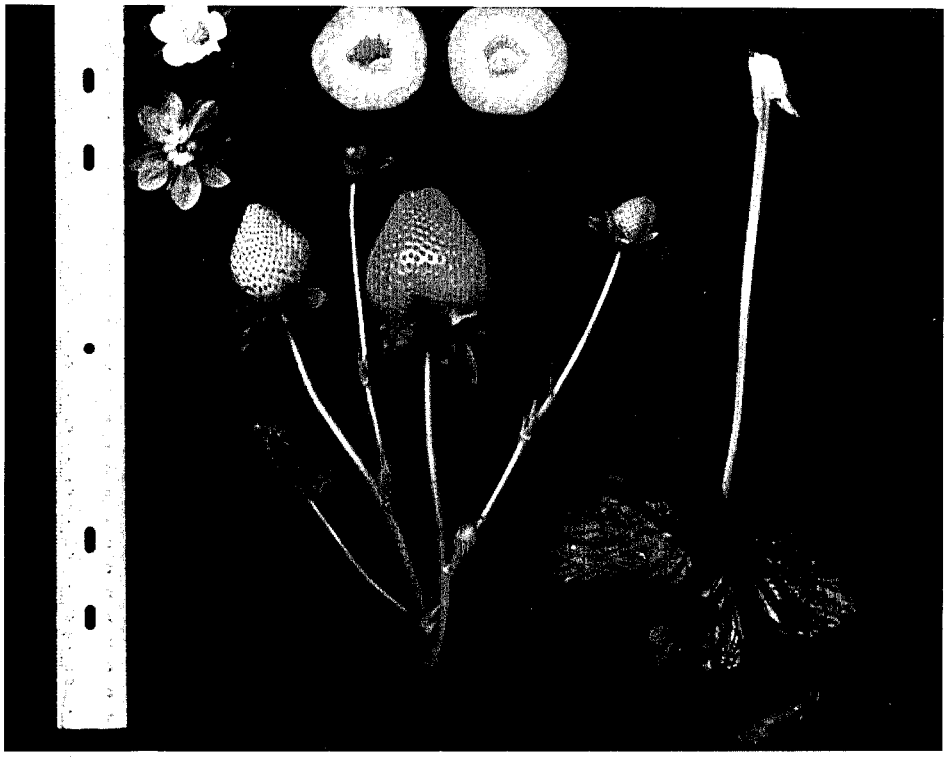

United States Patent [19]

Johnson, Jr. et al.

[11] Patent Number: Plant 7,024

[45] Date of Patent: Sep. 12, 1989

[54] STRAWBERRY PLANT 'COMMANDER'

[75] Inventors: Harold A. Johnson, Jr., Watsonville; David W. Small, Ventura; Amado Q. Amorao; Joseph I. Espejo, Jr., both of Watsonville, all of Calif.

[73] Assignee: Driscoll Strawberry Associates, Inc., Watsonville, Calif.

[21] Appl. No.: 220,851

[22] Filed: Jul. 18, 1988

[51] Int. Cl.[4] ..... A01H 5/00

[52] U.S. Cl. ..... Plt./49

[58] Field of Search ..... Plt./49

*Primary Examiner*—Robert E. Bagwill

*Attorney, Agent, or Firm*—Townsend and Townsend

[57] ABSTRACT

A new and distinct spring bearing variety of strawberry plant, characterized by its ability to produce a strong plant, but which remains in production consistently from April to October, if given adequate chilling before and after being planted.

The variety is particularly distinguished by its consistently good flavor, large calyx, large smooth and attractive fruit, and heavy total production. Its long shelf life also becomes a distinctive character. The dark and glossy leaflets are characters that help identify this new variety.

1 Drawing Sheet

This invention relates to a new and distinct variety of strawberry known as 'Commander' and which is the result of a cross of 'Crown' Variety, U.S. Plant Pat. No. 5,301 and 'Joe Reiter', U.S. Plant Pat. No. 5,300.

The seedlings resulting from the aforementioned cross were grown and asexually multiplied in Shasta County, Calif., and tested in the fruiting beds on the property of member growers of Driscoll Strawberry Associates, Inc. Clones of the seedlings are also held at the Propagation Nursery in Shasta County. One plant was selected from the aforementioned group of seedlings and further asexually reproduced by runners in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

In the drawings:

FIG. 1 illustrates plant part of the new variety, typical in size, shape and color during mid-May in central Coastal California when the variety is given adequate chilling before being dug and planted. A berry in cross sections illustrates flesh color and a characteristic core cavity. The inflorescence pictured illustrates typical branching and the relative size. In this illustration, the pedicel holding the primary berry originated from one of the pedicels holding a secondary berry, but many pedicels holding primary berries may also originate from the axil of peduncles or pedicels. This illustration shows a single bract leaflet with a deltoid shape originating at the union of the common peduncle and the axil of penduncles. These leaflet bracts may or may not be present. During May, when primaries of the main crop are ripening, there is a short common peduncle and only two secondary pedicels holding secondary berries that become large, and this is typical. The very wide calyx with individual large sepals is typical. The illustration also shows leaflets that are rugose, but which are quite glossy making this glossiness a distinguishing character. The serrations on the leaflets are medium in depth and show individual serrations with apexes not acute. The long petiole is free of bracts.

The large primary berry shown is smooth symmetrical and conic, but slightly wedged at the apex, free of ribbing or seedy tips, and this is typical. The hair on the pedicel is not visible in the illustration as it is not conspicuous and is irregularly parallel to the pedicel. The color of this primary berry is as dark as the 'Commander' usually reaches, and the flesh is light in color. The seeds held on this berry are held equal to the surface, which is generally typical, with the seed becoming slightly sunken on some fruit. The calyx is clasping on the primary, but one calyx of a secondary berry, when ripe, will be free of the fruit surface and the shoulders will not be as rounded as the fruit of the primary.

The novel winter planted spring variety named 'Commander' is adapted mainly to the central California coastal area where it shows the ability to produce a strong plant early. The early crown crop fruit comes during late March and April, and is acceptable, but not as attractive as its main crop which starts in early May. This main crop will start the first week of May if a full plastic mulch is applied under the plants during December or January. The plant of the 'Commander' is considered strong and large, becoming more vigorous and denser and larger than 'Swede' (plant patent application Ser. No. 862,347). The plant color of 'Commander' is dark, similar to 'Swede', but the leaflet gloss is distinctly glossier on the new variety. The crown diameter of the new variety is larger, and is attached to the soil more firmly than 'Swede'. The new variety is considered to be a lower chilling variety and it is necessary to give the 'Commander' less chilling before being planted than 'Swede', both for the desire of obtaining a plant that is not dense, with a minimum of runners, as well as to make certain the plant remains in a fruiting cycle through the summer and fall. The 'Commander' can also be distinguished from 'Swede' in that, during May, the leaflets are smaller and the petioles are longer and do not produce bracts. Hair on pedicels near berries is irregularly parallel to the pedicel in contrast to the direction of the hair on 'Swede', which is perpendicular to the pedicel. In contrast to 'Swede', the petiolules are shorter, the fruit is smoother, more conic, lighter in color, and the calyxes are larger in diameter and individual sepals are larger and more ovate to obovate in outline with a less acute tip.

This new variety is unique in that, while it is considered to have a low chilling strong plant, it has the ability to produce a continuous crop during the entire fruiting season in the central coastal area of California if the plant receives the correct amount of chilling before being planted. It has the ability to produce smooth, good appearing fruit with a minimum of malformed or seedy tipped berries. Only in late October does the fruit become necked at the calyx with non-fertilized achenes giving the fruit an elliptical outline rather than its normal round-shouldered conic appearance. Also, during July and August, fan or cockscomb shaped fruit may be produced. The fruit of this variety is consistently large and has the ability to produce long, thick pedicils, helping the variety to become adapted to the marketing of long-stems (where large attractive fruit is marketed with the pedicel remaining attached to the berry).

The glossy leaves are relatively tolerant to mycosphaerella leaf spot, but can be infected with powdery mildew and angular leaf spot. The fruit is susceptible to the anthracnose disease caused by the Colletotrichum fungus. The skin surface will crack easily from rain, but is not as susceptible to Botrytis as the 'Heidi' variety, U.S. Plant Pat. No. 3,123. Even though the fruit is large, its shelf life is good. Flavor panelists have given this friut high ratings and the fruit has a noticeable strawberry aroma. The plant is susceptible to injury from two-spotted mite, but will support large populations before showing injury. The fruit is detrimentally influenced by flower thrip in that the normal gloss is lost and becomes bronzed in appearance. This variety has not been tested against verticullium wilt and has not shown susceptibility to field inoculations of *Phytophthora cactorum.*

The varietal characteristics of the novel plant, described below in detail, were observed mainly during May in Watsonville, Calif., which is a coastal area near the Pacific Ocean. The measurements were made from plants that were planted in November and had been dug at a high elevation nursery in Shasta County, Calif. The color terminology is in accordance with the Munsell Color System.

Plant: Large and strong, and having a multiple crown. May become dense if given too much chilling before or after being planted or given too much fertilizer.

Leaves: Mostly medium to large, petioles on vigorously growing plants average 18 cm in length, measuring from the crown to the start of petiolules. The petiolules average 7 mm in length. Leaflets are moderately rugose with serrations that are moderately deep and cordate in outline with the apex not usually noticeably acute. The leaflet surface is noticeably glossy and dark as it reflects sun light. The upper side is 7.4GY2.3/4.0.

Isozymes in leaf extract:

Phosphoglucoispmerase (PGI): 5 Banded=A4*

Leucyl aminopetidase (LAP): 2 Banded=B3*

Phosphoglucomutase (PGM): 2 Banded=C42*

*=as designated by R. Bringhurst. This testing was done by Driscoll Strawberry Associates Laboratory following the procedure described in publication, "Electrophoretic Characterization of California Strawberry Cultivars" by Bringhurst — 1981.

Runners: Are vigorous and abundant at the nursery and also in the fruiting field when given more than the correct chilling for maximum fruit production.

Inflorescence: Medium to long in total length with the common peduncle short at the time of these measurements, but lengthens during the fruiting season. The pedicels holding primary and secondary fruit are long, averaging 10 to 13 cm in length. Diameter of pedicels is large becoming 3 mm in width. Usually, not more than two secondary berries develop with tertiaries uncommon. Tertiaries may be more common as the fruiting season progresses. The pedicel holding the primary berry may originate from the axil of secondary pedicels or peduncles, or from one of the secondary peduncles or pedicels. Hair on the pedicils 20 mm from the fruit is irregularly parallel to the pedicel. Flowers may or may not be visible above the plant in early May, but as the season progresses, flowers are more likely to be visible. Pollen is abundant on anthers of the main crop through September. There may be a lack of pollen on the first crown crop flowers and in late October and November.

Fruit: The fruit size of the crown crop is large, but may be elliptical in outline and not uniform with some irregularity in color. The main crop fruit, however, is consistently large, becoming 45 to 50 mm in length and slightly less in width with a minimum of irregular shapes, becoming mostly conic to long conic to long wedge, and October fruit may be necked as described in the USDA Bulletin 1043. There may be periods of production, however, when fan or cockscomb shaped fruit develop. Except for the late fall, the shoulders are round, with the calyx clasping the fruit. Folded seedy tips or other malformations are rare. Longitudinal ribs or furrows are also rare and the surface is considered glossy and smooth. Seed is usually held equal to the surface except during periods when heavy sheltered foliage is present, lack of light, and high nitrogen. Then the seed may be sunken. These same conditions may also cause albinism (a condition when there is a lack of red color on the fruit surface except near the seed). The flesh and skin are considered firm, except when albino fruit is being developed when skin is more prone to injury. Skin and flesh color are considered light, especially when fruit is completely shaded.

The core cavity is medium in size. The core is long and conspicuous when one is eating long stems. The dessert quality is very good. The surface color is 6.6R 2.9/9.7 and the inside color is 6.0R 5.5/15.7.

Calyx: The diameter is quite large, with many over 50 mm in width. Sepals are quite large and are ovate to wide elliptical and overlap each other and have a minimum of serrations. Some elliptical sepals have an acute apex, but the larger ovate sepals have a blunt apex. Color of sepals facing fruit is 0.6 to 2.8/6.5.

We claim:

1. The new and distinct variety of strawberry plant herein described and illustrated, and identified by the characteristics enumerated above.

* * * * *

UNITED STATES PATENT AND TRADEMARK OFFICE

CERTIFICATE OF CORRECTION

PATENT NO. : Plant 7,024

DATED : September 12, 1989

INVENTOR(S) : Harold A. Johnson, Jr. et al.

It is certified that error appears in the above-identified patent and that said Letters Patent is hereby corrected as shown below:

Column 3, line 61: change "C42*" to ---C4*---.

Signed and Sealed this

Fifth Day of February, 1991

*Attest:*

HARRY F. MANBECK, JR.

*Attesting Officer*

*Commissioner of Patents and Trademarks*